(12) United States Patent
Prausnitz et al.

(10) Patent No.: US 7,918,814 B2
(45) Date of Patent: Apr. 5, 2011

(54) METHOD FOR DRUG DELIVERY TO OCULAR TISSUE USING MICRONEEDLE

(75) Inventors: Mark R. Prausnitz, Atlanta, GA (US);
Ninghao Jiang, Alexandria, VA (US);
Henry F. Edelhauser, Atlanta, GA (US)

(73) Assignees: Georgia Tech Research Corporation, Atlanta, GA (US); Emory University, Atlanta, GA (US)

( * ) Notice: Subject to any disclaimer, the term of this patent is extended or adjusted under 35 U.S.C. 154(b) by 658 days.

(21) Appl. No.: 11/743,535

(22) Filed: May 2, 2007

(65) Prior Publication Data
US 2007/0260201 A1    Nov. 8, 2007

Related U.S. Application Data

(60) Provisional application No. 60/746,237, filed on May 2, 2006.

(51) Int. Cl.
*A61N 1/30* (2006.01)
(52) U.S. Cl. .......................................................... 604/19
(58) Field of Classification Search ...................... 604/19
See application file for complete search history.

(56) References Cited

U.S. PATENT DOCUMENTS

| | | | |
|---|---|---|---|
| 4,826,871 | A | 5/1989 | Gressel et al. |
| 4,966,773 | A | 10/1990 | Gressel et al. |
| 5,364,374 | A | 11/1994 | Morrison et al. |
| 5,547,467 | A | 8/1996 | Pliquett et al. |
| 5,667,491 | A | 9/1997 | Pliquett et al. |
| 5,911,223 | A | 6/1999 | Weaver et al. |
| 6,309,347 | B1 | 10/2001 | Takahashi et al. |
| 6,319,240 | B1 | 11/2001 | Beck |
| 6,334,856 | B1 | 1/2002 | Allen et al. |
| 6,397,849 | B1 | 6/2002 | Bowman et al. |
| 6,503,231 | B1 | 1/2003 | Prausnitz et al. |

(Continued)

FOREIGN PATENT DOCUMENTS

WO    00/07530    2/2000

(Continued)

OTHER PUBLICATIONS

Beer et al., Photographic Evidence of Vitreous Wicks After Intravitreal Injections, Retina Today 2(2): 24-39 (2007).

(Continued)

*Primary Examiner* — Nicholas D Lucchesi
*Assistant Examiner* — Pritesh Patel
(74) *Attorney, Agent, or Firm* — Sutherland Asbill & Brennan LLP

(57) ABSTRACT

Methods and devices are provided for administering a drug to a patient's eye. The methods include (a) inserting a hollow microneedle into the sclera or corneal stroma without penetrating across the sclera or corneal stroma; and (b) infusing a fluid drug formulation through the microneedle and into the sclera or cornea. It further may include partially retracting the microneedle before infusion to enhance delivery. Alternatively, the methods may include (a) inserting a solid microneedle into the sclera or corneal stroma without penetrating across the sclera or corneal stroma, wherein the solid microneedle comprises a first quantity of a drug formulation and inserting causes the solid microneedle to form a pocket in the sclera or corneal stroma; and (b) releasing the drug formulation into the pocket to form a drug depot, whereby a drug is released from the depot. The methods and devices may include an array of multiple microneedles.

52 Claims, 7 Drawing Sheets

U.S. PATENT DOCUMENTS

| | | |
|---|---|---|
| 6,524,581 B1 | 2/2003 | Adamis |
| 6,611,707 B1 | 8/2003 | Prausnitz et al. |
| 6,743,211 B1 | 6/2004 | Prausnitz et al. |
| 6,773,916 B1 | 8/2004 | Thiel et al. |
| 7,226,439 B2 | 6/2007 | Prausnitz et al. |
| 2002/0082527 A1 | 6/2002 | Liu et al. |
| 2002/0082543 A1* | 6/2002 | Park et al. ............. 604/21 |
| 2003/0083645 A1 | 5/2003 | Angel et al. |
| 2004/0265365 A1 | 12/2004 | Daddona et al. |
| 2005/0137525 A1 | 6/2005 | Wang et al. |
| 2005/0209565 A1 | 9/2005 | Yuzhakov et al. |
| 2006/0013859 A1 | 1/2006 | Yamada et al. |
| 2006/0084942 A1 | 4/2006 | Kim et al. |
| 2006/0086689 A1 | 4/2006 | Raju |
| 2007/0073197 A1 | 3/2007 | Prausnitz et al. |

FOREIGN PATENT DOCUMENTS

| | | |
|---|---|---|
| WO | 00/07565 | 2/2000 |
| WO | 03/024507 | 3/2003 |
| WO | 2006/004595 | 1/2006 |
| WO | 2006/128034 | 11/2006 |
| WO | WO 2006/128034 A1 * | 11/2006 |
| WO | 2006/138719 | 12/2006 |

OTHER PUBLICATIONS

Edwards & Prausnitz, Fiber matrix model of sclera and corneal stroma for drug delivery to the eye, AIChE Journal 44(1): 214-25 (1998).

Jiang et al, Measurement and Prediction of Lateral Diffusion within Human Sclera, Investigative Ophthalmology & Visual Science 47(7): 3011-3016 (2006).

Jiang et al., Coated Microneedles for Drug Delivery to the Eye, Investigative Ophthalmology & Visual Science 48 (9): 4038-4043 (2007).

McCallister et al., Microfabricated needles for transdermal delivery of macromolecules and nanoparticles: Fabrication methods and transport studies, Proc. Nat'l Acad. Sci USA 100(24): 13755-60 (2003).

Wang et al., Minimally Invasive Extraction of Dermal Interstitial Fluid for Glucose Monitoring Using Microneedles, Diabetes Technology & Therapeutics 7(1): 131-141 (2005).

ISR/Written Opinion for PCT/US2007/068055.

* cited by examiner

METHOD FOR DRUG DELIVERY TO OCULAR TISSUE USING MICRONEEDLE

CROSS REFERENCE TO RELATED APPLICATIONS

This application claims benefit of U.S. Provisional Application No. 60/746,237, filed May 2, 2006. The application is incorporated herein by reference.

STATEMENT REGARDING FEDERALLY SPONSORED RESEARCH OR DEVELOPMENT

This invention was made with U.S. government support under Contract No. 8 RO1 EB00260-03 and Contract No. R24EY017045-01, which were awarded by the National Institute of Health. The U.S. government has certain rights in the invention.

BACKGROUND OF THE INVENTION

This invention is generally in the field of ophthalmic therapies, and more particularly to the use of microneedles for local drug delivery to and/or diagnostic sensing in ocular tissues.

The delivery of drug to the eye is extremely difficult, particularly delivery of macromolecules and delivery to the back of the eye. Many inflammatory and proliferative diseases in the posterior region of the eye require long term pharmacological treatment. Examples of such diseases include macular degeneration and diabetic retinopathy. It is difficult to deliver effective doses of drug to the back of the eye using conventional delivery methods such as topical application, which has poor efficacy, and systemic administration, which often causes significant side effects. (Geroski & Edelhauser, *Invest. Ophthalmol. Vis. Sci.* 41:961-64 (2000)). For example, while eye drops are useful in treating conditions affecting the exterior surface of the eye or tissues at the front of the eye, the eye drops cannot penetrate to the back of the eye, as may be required for the treatment of various retinal diseases.

Direct injection into the eye, using conventional needles and syringes is often effective, but requires professional training and raises concerns about safety. (Maurice, *J. Ocul Pharmacol. Ther.* 17:393-401 (2001)). It also would be desirable to be able to minimize the number and/or frequency of eye injection treatments needed to effect delivery of a selected quantity of drug.

It therefore would be desirable to provide better, safer, more effective techniques for the direct delivery of therapeutic agents to eye tissues. It also would be desirable to provide devices useful in such techniques which can be relatively inexpensive to produce and use. It further would be desirable to provide methods for pinpoint delivery of drug to scleral or corneal tissues.

SUMMARY OF THE INVENTION

Methods are provided for administering a drug to an eye of a patient. The methods may be used, for example, in the treatment of uveitis, glaucoma, diabetic macular edema, age-related macular degeneration, corneal infection, or cytomegalovirus retinitis.

In one aspect, a method is provided that includes the steps of (a) inserting at least one hollow microneedle into the sclera or corneal stroma of the eye without penetrating across the sclera or corneal stroma; and (b) infusing a fluid drug formulation through the at least one hollow microneedle and into the sclera or cornea, wherein the fluid drug formulation comprises a drug. In a certain embodiment, this method further includes after the insertion step and before and/or during the step of infusing, partially retracting the at least one hollow microneedle from the sclera or corneal stroma. In a certain embodiment, the steps of inserting and retracting the at least one hollow microneedle form a pocket in the sclera or corneal stroma.

The step of infusing may be performed after the step of partially retracting the at least one microneedle out of the sclera or corneal stroma. The step of infusing may include driving the fluid drug formulation using a pressure gradient or an electric field.

The step of infusion may create a drug depot in the sclera or corneal stroma for sustained release of the drug from the drug depot after the step of infusion is completed. In certain embodiments, the drug from the drug depot may be delivered to choroidal or retinal tissues. In certain embodiments, the drug may be delivered to the ciliary body, the trabecular meshwork, the aqueous humor, or the vitreous humor.

In a preferred embodiment, the method may include the use of an array of two or more microneedles. For example, the step of inserting may further comprise substantially simultaneously inserting a second hollow microneedle into the sclera or corneal stroma without penetrating across the sclera or corneal stroma, and the step of infusing may further comprise infusing the fluid drug formulation through the second hollow microneedle and into the sclera or corneal stroma. The at least one (i.e., first) hollow microneedle and the second hollow microneedle are part of a device having an array of two or more microneedles.

In one embodiment the fluid drug formulation comprises a suspension of microparticles or nanoparticles for controlled release of the drug. In one embodiment, the fluid drug formulation further includes an agent effective to degrade collagen or glycosaminoglycan (GAG) fibers in the sclera or corneal stroma. This agent may be, for example, an enzyme, such a hyaluronidase, a collagenase, or a combination thereof.

In another aspect, a method is provided that includes the steps of (a) inserting at least one solid microneedle into the sclera or corneal stroma of the eye without penetrating across the sclera or corneal stroma, wherein the at least one solid microneedle comprises a first quantity of a drug formulation and the step of inserting causes the at least one solid microneedle to form a pocket in the sclera or corneal stroma; and (b) releasing at least part of the first quantity of the drug formulation into the pocket to form a drug depot in the sclera or corneal stroma, whereby a drug in the drug formulation subsequently is released from the drug depot. In one embodiment, the method may include driving the drug into or through the sclera or corneal stroma using an electric field or acoustic energy. In certain embodiments, the drug from the drug depot may be delivered to choroidal or retinal tissues. In certain embodiments, the drug may be delivered to posterior chamber tissue or to anterior chamber tissue.

In a preferred embodiment, the method may include the use of an array of two or more microneedles. For example, the step of inserting may further comprise substantially simultaneously inserting a second solid microneedle into the sclera or corneal stroma without penetrating across the sclera or corneal stroma, wherein (i) the second solid microneedle includes a second quantity of the drug formulation, and (ii) the step of inserting causes the second solid microneedle to form a second pocket in the sclera or corneal stroma; and the step of releasing further includes releasing the second quantity of the drug formulation into the second pocket to form a second drug depot in the sclera or corneal stroma, whereby subsequently the drug is released from the second drug depot into the eye. The at least one (i.e., first) solid microneedle and the second solid microneedle are part of a device having an array of two or more microneedles.

In a preferred embodiment, the method further includes completely withdrawing the at least one solid microneedle from the sclera or corneal stroma after the step of inserting, wherein the drug depot provides sustained release of the drug after the at least one solid microneedle has been completely withdrawn.

In one embodiment, the at least one solid microneedle comprises a solid or semi-solid coating that includes the drug formulation. In one case, the step of releasing comprises at least partially dissolving the coating off of the at least one solid microneedle into fluids present in the sclera or corneal stroma. In another embodiment, the step of releasing includes breaking or dissolving all or part of the at least one solid microneedle off of a base to which the at least one solid microneedle is connected prior to said breaking or dissolving. In this case, the drug formulation is broken off or dissolves off with or as part of the microneedle. In these embodiments of the method, the drug formulation may include microparticles or nanoparticles which comprise a drug for controlled release.

In one embodiment, the hollow or solid microneedle is rotated or vibrated during the step of inserting. In another embodiment, the hollow or solid microneedle is inserted into the surface of the sclera or corneal stroma at an angle of about 90 degrees.

In another aspect, a method of extraction from a tissue of the eye is provided that includes the steps of (a) inserting at least one microneedle into the sclera or corneal stroma, without penetrating across the sclera or corneal stroma; and (b) withdrawing a biological fluid, tissue, or molecule sample from the sclera or corneal stroma with the at least one microneedle.

In yet another aspect, a microneedle device is provided for delivery of a drug to the eye. In one embodiment, the device includes an array of two or more microneedles extending from a base; means for controllably inserting the two or more microneedles into the sclera or corneal stroma without penetrating across the sclera or corneal stroma; and means for depositing a drug formulation in the sclera or corneal stroma to form a drug depot for subsequent release to an ocular tissue.

In certain embodiments, the two or more microneedles may be hollow or solid. In various embodiments, the hollow or solid microneedle may be made of metal or a polymer.

In one embodiment, the drug depot provides extended or sustained release of a drug. In one embodiment, the drug formulation comprises microparticles or nanoparticles which provide controlled release of the drug.

The means for depositing may include a coating on the two or more microneedles, wherein the coating comprises the drug formulation. In one embodiment, the coating may be solid or semi-solid. The coating may be at least partially soluble in fluids present in the sclera or corneal stroma. In another embodiment, all or part of the two or more microneedles are adapted to break or dissolve off of the base in the sclera or cornea.

In one embodiment, the two or more microneedles extend from the base at an angle of about 90 degrees to provide approximately perpendicular insertion of the microneedles into the surface of the sclera or corneal stroma. In one embodiment, the base has either a fixed radius of curvature substantially the same as the radius of curvature of surface of a sclera or corneal stroma, or is elastically deformable to fit the radius of curvature of surface of a sclera or corneal stroma.

In one embodiment with hollow microneedles, the means for depositing comprises a fluid drug formulation, a source reservoir for the fluid drug formulation, and an infusion means for driving the fluid drug formulation from the source reservoir into the pocket. In a certain embodiment, the infusion means may include a pump or syringe. In a preferred embodiment, the fluid drug formulation comprises a suspension of microparticles or nanoparticles which comprise a drug for controlled release.

In one embodiment, the portion of the microneedle that is designed to insert into the sclera or corneal stoma has a maximum cross-sectional width or diameter between 50 microns and 400 microns. In one embodiment, the portion of the microneedle that is designed to insert into the sclera or corneal stoma has length between 50 microns and 1000 microns.

In one particular embodiment, a microneedle device is provided for delivery of a drug to the eye that includes at least one solid microneedle extending from a base; means for controllably inserting the at least one solid microneedle into the sclera or corneal stroma without penetrating across the sclera or corneal stroma; and a drug formulation which comprises a drug, wherein the device is adapted to deposit the drug formulation into the sclera or corneal stroma to form a drug depot for controlled release of the drug to an ocular tissue.

DETAILED DESCRIPTION OF PREFERRED EMBODIMENTS

Figure 1A:
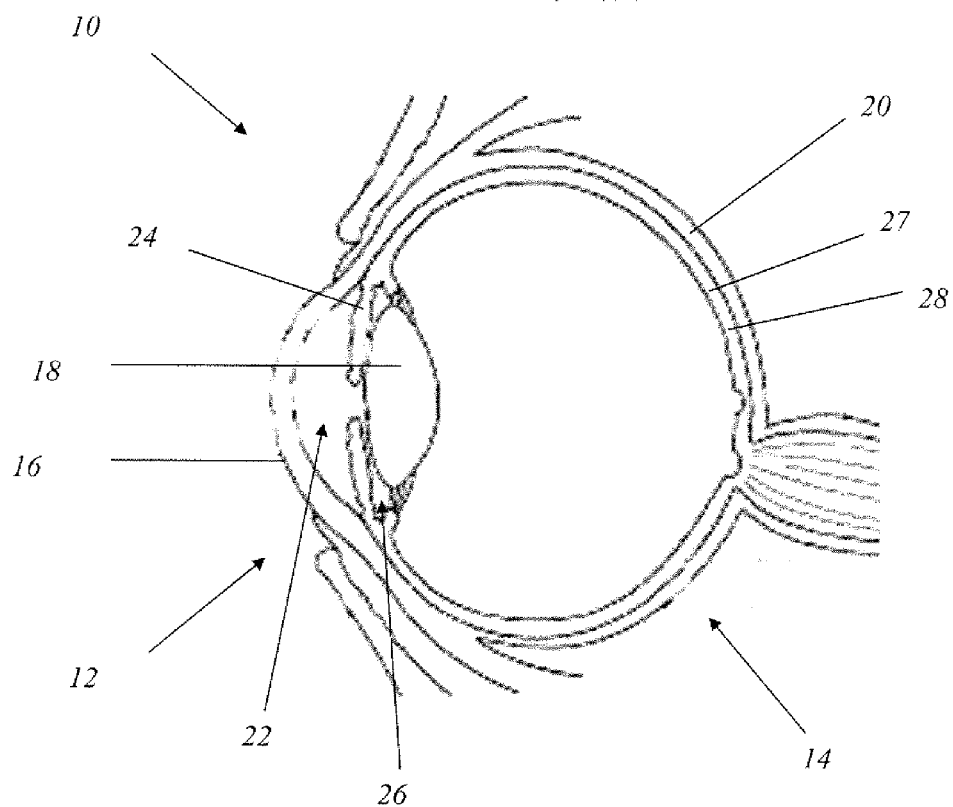
FIGS. 1A, 1B, and 1C are cross-sectional illustrations of the tissue structures of a human eye. The eye as a whole (1A), a close-up of the cornea (1B), and a close-up of the sclera and associated tissues (1C) are shown.

In one aspect of the invention, microneedle devices and methods of use have been developed to enhance the delivery of a drug to the eye, enabling drug to be locally administered in useful quantities. In one advantageous and exemplary embodiment of the methods described herein, sustained delivery of a drug is achieved from a drug depot created in the sclera or cornea with the microneedle and a drug formulation. The microneedle is able to precisely locate the drug in the sclera or corneal tissue for subsequent local delivery to nearby tissues in need of treatment. The drug may be released for an extended period, e.g., several hours, after the microneedle has been inserted and withdrawn, providing increased bioavailability of the drug relative, for example, to delivery by topical application of the drug formulation to ocular tissue surfaces. The method advantageously includes precise control of the depth of insertion into the ocular tissue, so that the microneedles do not cross into the anterior chamber underlying the cornea or penetrate across the sclera to contact underlying tissue layers, such as choroid and retina tissues. Microneedles enable this to be done in a minimally invasive manner.

Advantageously, an array of microneedles may be provided so that multiple drug depots can be deposited in the sclera or cornea with a single application/treatment. Moreover, the spacing of the microneedles in the array beneficially can "spread" the delivery of drug over a larger tissue area in a single administration as compared to a single administration using previously known single needle devices. It may be important to minimize the distance the drug must diffuse from the depot to reach tissues in need of treatment. It would be advantageous to accomplish the treatment with as few injection events as possible.

As used herein, the terms "comprise," "comprising," "include," and "including" are intended to be open, non-limiting terms, unless the contrary is expressly indicated.

Methods of Using the Microneedle

The microneedle devices described herein may be used to deliver drug formulations to the eye, particularly for the treatment, diagnosis, or prevention of ocular diseases. A wide range of ocular diseases and disorders may be treated by the methods and devices described herein. Non-limiting examples of ocular diseases include uveitis, glaucoma, diabetic macular edema or retinopathy, macular degeneration, corneal infection, cytomegalovirus retinitis, and dry eye (i.e., keratoconjunctivitis sicca).

The microneedles can be used to target delivery to specific tissues or regions within the eye. For example, targeted delivery to the anterior chamber of the eye may be achieved by microneedle delivery of a drug formulation into the cornea. As another example, targeted delivery to the posterior segment may be achieved by microneedle delivery of a drug formulation to the sclera. Injection may be performed relatively quickly, e.g., in less than one minute, and possibly facilitated by having the patient look all the way to the left or right and then inserting microneedles at, or posterior to, the equator. In various embodiments, the methods may be designed for drug delivery specifically to the ciliary body, the trabecular meshwork, the aqueous humor, or the vitreous humor.

Figure 1B:
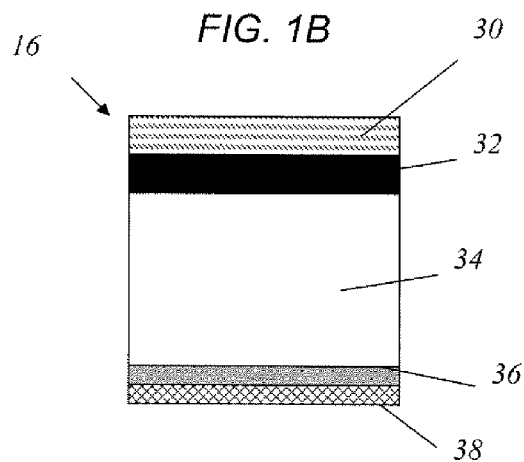
Figure 1C:
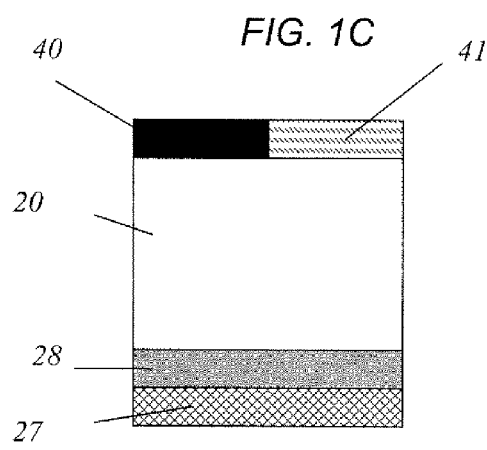

As used herein, "ocular tissue" and "eye" 10 include both the anterior segment 12 of the eye (i.e., the portion of the eye in front of the lens) and the posterior segment 14 of the eye (i.e., the portion of the eye behind the lens), as illustrated in FIG. 1A. The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The exposed portion of the sclera 20 on the anterior segment 12 of the eye is protected by a clear membrane referred to as the conjunctiva (not shown). Underlying the sclera 20 is the choroid 28 and the retina 27. FIG. 1B illustrates the cornea 16, which is composed of the epithelium 30, the Bowman's layer 32, the stroma 34, the Descemet's membrane 36, and the endothelium 38. FIG. 1C illustrates the sclera 20 with surrounding Tenon's Capsule 40 or conjunctiva 41, choroid 28, and retina 27.

The method of administering a drug to the eye generally comprises the steps of inserting a microneedle into the ocular tissue and depositing a drug formulation into the ocular tissue. In a particular embodiment, at least one microneedle is inserted into the sclera or corneal stroma of the eye without penetrating across the scleral or corneal stroma. In one embodiment, which may be particularly useful with hollow microneedles, the method of administering a drug to the eye may further include partially retracting the hollow microneedle after the insertion step and before and/or during the depositing of the drug formulation.

Figure 5A:
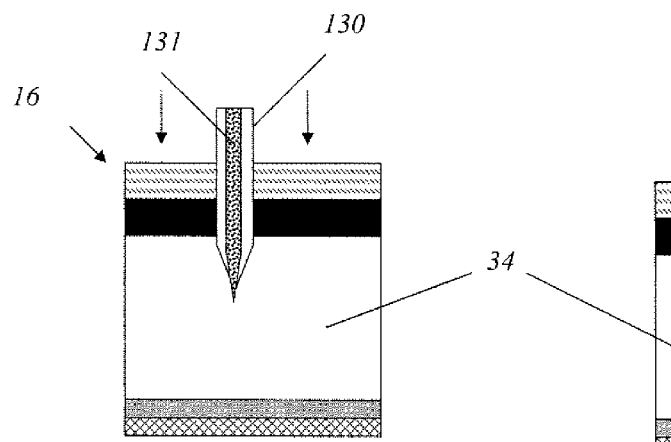
FIGS. 5A and 5B illustrate an embodiment of a process for using a hollow microneedle to deliver drug into the corneal stroma of an eye, where the process includes partial retraction of the hollow microneedle and infusion of a fluid drug formulation.
Figure 5B:
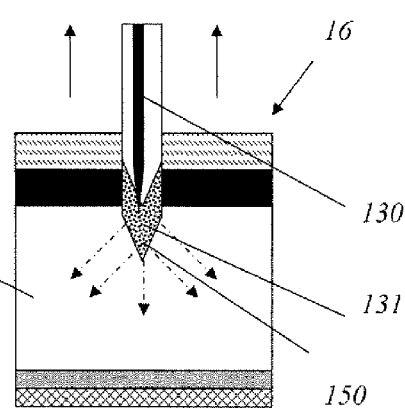

In a particular embodiment, the partial retraction of the microneedle occurs prior to the step of infusing the fluid drug formulation into the ocular tissue. This insertion/retraction step forms a pocket and beneficially permits the fluid drug formulation to flow out of the microneedle unimpeded or less impeded by ocular tissue at the opening at the tip portion of the microneedle. FIG. 5A shows a hollow microneedle 130 inserted into the corneal stroma 34, with drug formulation 131 temporarily positioned in the hollow bore of the microneedle. (The fluid communication to a reservoir of the fluid drug formulation is not shown.) FIG. 5B shows the microneedle 130 following partial retraction to form pocket 150 and infusion of fluid drug formulation 131 therein. Arrows show further transport of the drug formulation into the tissue.

The microneedle optionally may be part of an array of two or more microneedles such that the method further includes inserting at least a second microneedle into the sclera or corneal stroma without penetrating across the sclera or corneal stroma. The method of inserting the microneedle and/or depositing a drug formulation optionally may include rotating the microneedle or vibrating the microneedle during the insertion step or the release step, or during both steps.

Importantly, the depth of insertion into the ocular tissue is precisely controlled. In one preferred embodiment, the one or more microneedles are inserted within the cornea, neither across nor entering the anterior chamber. In another preferred embodiment, the one or more microneedles are inserted within the sclera without penetration/contacting underlying tissue layers, such as choroid and retina tissues. (The drug depot formed using the microneedle and drug formulation can, however, deliver drug to these underlying tissues.) Essentially any method can be used to control the insertion depth. In one embodiment, the microneedles are designed to have a length approximately equal to the desired penetration depth. In another embodiment, the microneedles are designed to have a length longer than the desired penetration depth, but the microneedles are controllably inserted only part way into the tissue. Partial insertion may be controlled by the mechanical properties of the tissue, which bends and dimples during the microneedle insertion process. In this way, as a microneedle is inserted into the tissue, its movement partially elastically deforms the tissue and partially penetrates into the tissue. By controlling the degree to which the tissue deforms, the depth of microneedle insertion into the tissue can be controlled. In another embodiment, a microneedle is inserted into the tissue using a rotational/drilling technique and/or a vibrating action. In this way, the microneedle can be inserted to a desired depth by, for example, drilling the microneedles a desired number of rotations, which corresponds to a desired depth into the tissue. See, e.g., U.S. Patent Application Publication No. 20050137525 A1 to Wang et al., which is incorporated herein by reference, for a description of drilling microneedles.

The amount of drug delivered within the ocular tissue may be controlled, in part, by the type of microneedle used and how it is used. In one exemplary embodiment, a hollow microneedle is inserted into the ocular tissue and progressively retracted from the ocular tissue after insertion to deliver a fluid drug, where after achieving a certain dosage, the delivery could be stopped by deactivating the fluid driving force, such as pressure (e.g., from a mechanical device such as a syringe) or an electric field, to avoid leakage/uncontrolled deliver of drug.

Methods of depositing or releasing the drug formulation into ocular tissue during microneedle insertion may occur in different ways, depending for example on whether the microneedle is solid or hollow. The methods may include (a) infusing a fluid drug formulation through a hollow microneedle (e.g., driving the drug formulation from a source reservoir into the ocular tissue by a pressure gradient (e.g., pumping, syringe) or an electric field (e.g., iontophoresis) or another externally applied energy (e.g., ultrasound/acoustic energy), (b) dissolving, at least in part, a coating of a drug formulation off of a solid (or hollow) microneedle, (c) detaching, at least in part, a coating of a drug formulation (e.g., as a substantially intact sleeve or in fragments) off of a solid (or hollow) microneedle, (d) breaking or dissolving a solid (or hollow) microneedle off of a base to which the microneedle is integrally formed or is connected), or (e) a combination of (a) through (d).

Figure 6A:
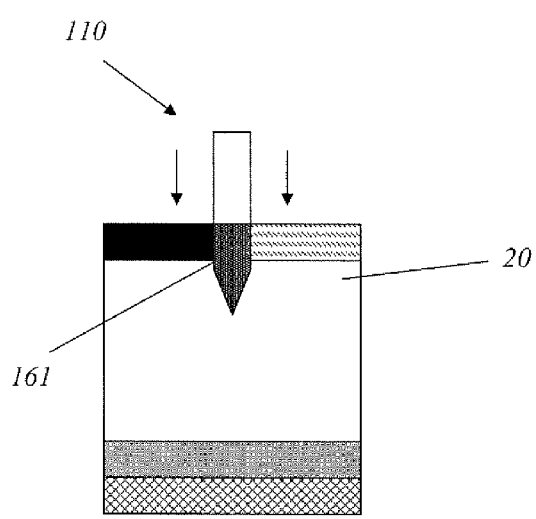
FIGS. 6A and 6B illustrate an embodiment of a process for inserting a solid microneedle which has a drug formulation coating, into the sclera of an eye.
Figure 6B:
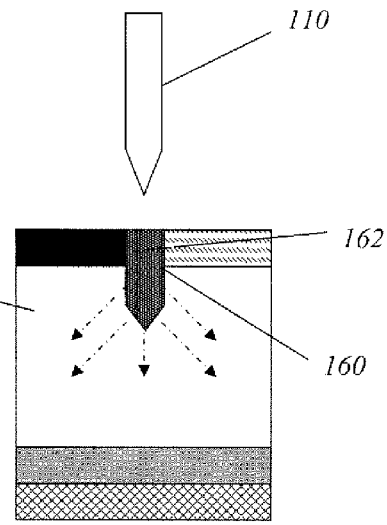

FIG. 6A shows solid microneedle 110 with drug formulation coating 161 inserted into the sclera 20. FIG. 6B shows the microneedle 110 following complete withdrawal of the microneedle 110 from the tissue, to form pocket 160 into which the drug formulation has been released from the microneedle and deposited to form a drug depot 162 from which the drug subsequently is released (as shown by arrows from the depot).

In a particular embodiment, the microneedle deposits a drug formulation within the cornea or sclera for controlled (i.e., sustained or extended) release of a drug to one or more ocular tissues surrounding the depot. This "sustained release" or "extended release" is generally more prolonged than that obtainable by topical application of the drug formulation to the ocular tissue. In a particular embodiment, the drug depot provides extended or sustained release of the drug formulation after the at least one microneedle is withdrawn from the ocular tissue. This delivery method can be particularly advantageous with ocular tissues, where it is desirable for the insertion and withdrawal process to occur over as short a period as possible to minimize patient discomfort—in contrast to transdermal microneedle patch applications, where patches may more likely be worn (with microneedles inserted) over an extended period without patient discomfort.

In a preferred embodiment wherein an array of two or more microneedles are inserted into the ocular tissue, each microneedle may form an independent pocket in the ocular tissue into or through which a drug formulation may be deposited. In a particular embodiment, the drug formulation of each of the two or more microneedles may be identical to or different from one another, in drug, formulation, volume/quantity of drug formulation, or a combination of these parameters. In one case, different types of drug formulations may be deposited into the two or more pockets. For example, inserting a second solid microneedle comprising a second drug formulation into the ocular tissue will form a second pocket in the ocular tissue, and releasing of the second drug formulation into or through the second pocket will form a second drug depot from which the second drug formulation subsequently may be released.

In one embodiment, the drug formulation for delivery into the eye is in the form of or includes polymeric nanoparticles or microparticles encapsulating the active agent. Nanoparticle or microparticle encapsulation techniques are well known in the art. In another embodiment, the drug formulation is one which undergoes a phase change upon administration. For instance, a liquid drug formulation may be injected through hollow microneedles into the ocular tissue, where it then gels within the ocular tissue and the drug diffuses out from the gel for controlled release.

In another embodiment, the microneedle is formed of a drug encapsulated within a polymer, which can be implanted into the ocular tissue for drug release upon degradation/dissolution of the microneedle. The polymer may be a biodegradable one, such as poly(lactide-co-glycolide) (PLGA). In a specific case, the microneedle or the tip portion thereof may be intentionally broken off in the sclera or cornea, and subsequently will biodegrade and release drug.

In still another embodiment, the microneedle is formed of metal and coated with a drug formulation, which delivers the drug by dissolution/diffusion upon insertion into the ocular tissue. In a particular embodiment, the drug coating is soluble in the fluids present in the ocular tissue, but is designed to have a dissolution rate that is sufficiently slow to avoid dissolution in the tear film during insertion of the microneedle device, thereby preventing excess/premature loss of drug.

The microneedle devices described herein also may be used to remove substances, such as a fluid, tissue, or molecule sample, from the eye. For example, the microneedle may be used to remove intraocular fluid from the eye to treat glaucoma. The fluid may be withdrawn through a hollow microneedle while the microneedle remains in an inserted position in the ocular tissue. Alternatively, the fluid may flow out through an aperture left in the ocular tissue after the solid or hollow microneedle has been withdrawn from the tissue. Tissue may be removed by a coring method related to conventional biopsies. Molecules may be removed by binding a molecule to the microneedle. The binding may be a selective chemical binding.

The microneedle devices described herein also may be adapted to use the one or more microneedles as a sensor to detect analytes, electrical activity, and optical or other signals. The sensor may include sensors of pressure, temperature, chemicals, and/or electromagnetic fields (e.g., light). Biosensors can be located on the microneedle surface, inside a hollow or porous microneedle, or inside a device in communication with the body tissue via the microneedle (solid, hollow, or porous). The microneedle biosensor can be any of the four classes of principal transducers: potentiometric, amperometric, optical, and physiochemical. In one embodiment, a hollow microneedle is filled with a substance, such as a gel, that has a sensing functionality associated with it. In an application for sensing based on binding to a substrate or reaction mediated by an enzyme, the substrate or enzyme can be immobilized in the needle interior. In another embodiment, a wave guide can be incorporated into the microneedle device to direct light to a specific location, or for detection, for example, using means such as a pH dye for color evaluation. Similarly, heat, electricity, light or other energy forms may be precisely transmitted to directly stimulate, damage, or heal a specific tissue or for diagnostic purposes.

The Microneedle Device

In an exemplary embodiment, the microneedle device includes a base from which one or more microneedles extend, typically in a direction normal (i.e., perpendicular) to the base. The microneedle can be hollow or solid. As used herein, the term "hollow" includes a single, straight bore through the center of the microneedle, as well as multiple bores, bores that follow complex paths through the microneedles, multiple entry and exit points from the bore(s), and intersecting or networks of bores. That is, a hollow microneedle has a structures that includes one or more continuous pathways from the base of the microneedle to an exit point in the shaft and/or tip portion of the microneedle distal to the base. The microneedle structure can be porous or non-porous. Drug can be coated onto the microneedle; integrated into the structure of, or pores in, the microneedle; passed through bores/apertures or channels in the microneedle, or a combination thereof. The base may be substantially planar or it may be curved, for example, in the shape of the ocular tissue surface at the site of injection. The base may be rigid, or in a preferred embodiment flexible to conform to the shape of the ocular tissue at the site for injection.

Figure 2:
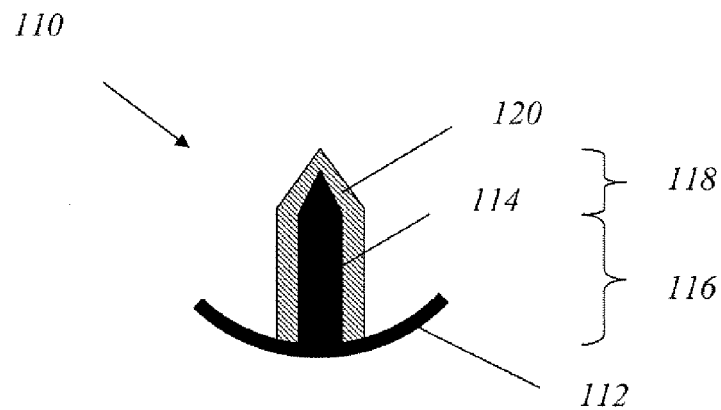
FIG. 2 is a cross-sectional view of a solid microneedle having a drug-comprising coating, according to one embodiment.
Figure 3:
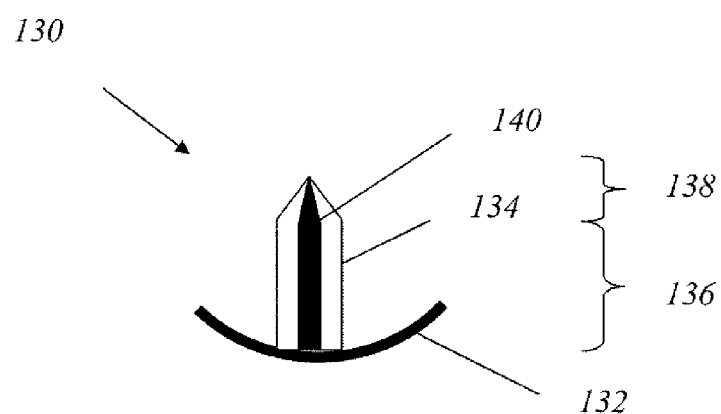
FIG. 3 is a cross-sectional view of a hollow microneedle according to one embodiment.
Figure 4:
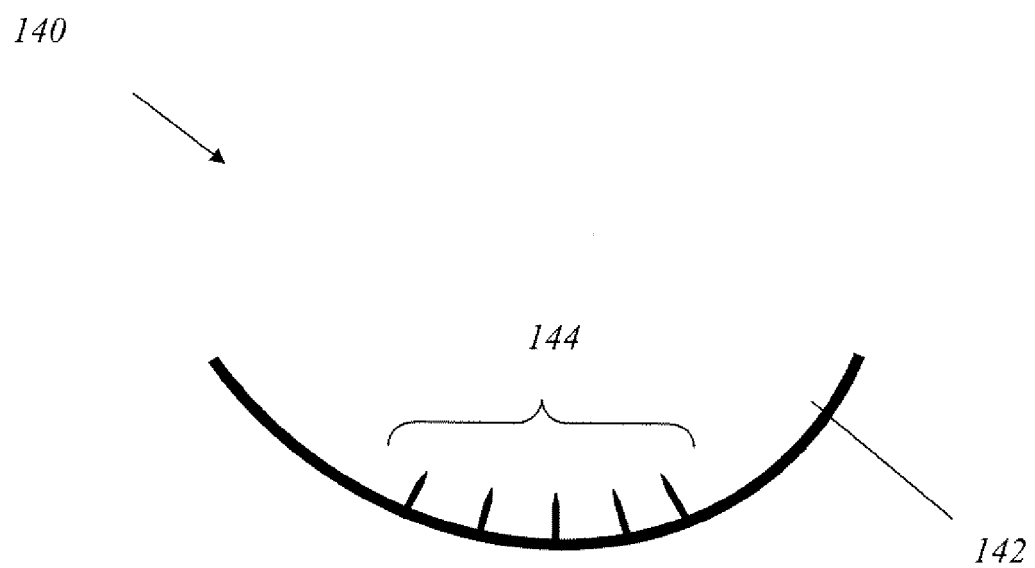
FIG. 4 is a cross-sectional view of an array of solid microneedles according to one embodiment.

FIGS. 2 and 3 illustrate two exemplary embodiments of the microneedle devices. In one embodiment, illustrated in FIG. 2, the microneedle device 110 includes a base 112 and a solid microneedle 114, which is coated with a drug formulation 120. The solid microneedle 114 includes a proximal portion 116 and a tip portion 118. In another embodiment, illustrated in FIG. 3, the microneedle device 130 includes a base 132 and a hollow microneedle 134 which has a bore 140 through which a fluid drug formulation (not shown) can be delivered to the eye or through which a biological fluid can be withdrawn from the eye. The hollow microneedle 134 includes a proximal portion 136 and a tip portion 138. FIG. 4 illustrates one possible embodiment of a microneedle array device 140, which includes a base 142 from which solid microneedles 144 (five are shown) extend.

The microneedle can be formed/constructed of different biocompatible materials, including metals, glasses, semiconductor materials, ceramics, or polymers. Examples of suitable metals include pharmaceutical grade stainless steel, gold, titanium, nickel, iron, gold, tin, chromium, copper, and alloys thereof. The polymer can be biodegradable or non-biodegradable. Examples of suitable biocompatible, biodegradable polymers include polylactides, polyglycolides, polylactide-co-glycolides (PLGA), polyanhydrides, poly-orthoesters, polyetheresters, polycaprolactones, polyesteramides, poly(butyric acid), poly(valeric acid), polyurethanes and copolymers and blends thereof. Representative non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Biodegradable microneedles can provide an increased level of safety compared to non-biodegradable ones, such that they are essentially harmless even if inadvertently broken off into the ocular tissue. This applies whether the microneedles contain molecules for delivery or serve merely a conduit function.

The microneedle can have a straight or tapered shaft. In one embodiment, the diameter of the microneedle is greatest at the base end of the microneedle and tapers to a point at the end distal the base. The microneedle can also be fabricated to have a shaft that includes both a straight (i.e., untapered) portion and a tapered portion. The microneedles can be formed with shafts that have a circular cross-section in the perpendicular, or the cross-section can be non-circular. The tip portion of the microneedles can have a variety of configurations. The tip of the microneedle can be symmetrical or asymmetrical about the longitudinal axis of the shaft. The tips may be beveled, tapered, squared-off or rounded. The tip portion generally has a length that is less than 50% of the total length of the microneedle.

The dimensions of the microneedle, or array thereof, are designed for the particular way in which it is to be used. The length typically is selected taking into account both the portion that would be inserted into the ocular tissue and the (base) portion that would remain uninserted. The cross-section, or width, is tailored to provide, among other things, the mechanical strength to remain intact for the delivery of the drug or for serving as a conduit for the withdrawal of biological fluid, while being inserted into the skin, while remaining in place during its functional period, and while being removed (unless designed to break off, dissolve, or otherwise not be removed). In various embodiments, the microneedle may have a length of about 50 µm to about 2000 µm. In another particular embodiment, the microneedle may have a length of about 150 µm to about 2000 µm, about 300 µm to about 2000 µm, about 300 µm to about 1500 µm, about 300 µm to about 1000 µm, or about 300 to about 750 µm. In one embodiment, the length of the microneedle is about 500 µm. In various embodiments, the base portion of the microneedle has a maximum width or cross-sectional dimension of about 20 µm to about 500 µm, about 50 µm to about 400 µm, or about 100 µm to about 250 µm. For a hollow microneedle, the maximum outer diameter or width may be about 50 µm to about 400 µm, with an aperture diameter of about 5 µm to about 100 µm. The microneedle may be fabricated to have an aspect ratio (width:length) of about 1:1.5 to about 11:10. Other lengths, widths, and aspect ratios are envisioned.

In various embodiments, the microneedle device includes a single microneedle or an array of two or more microneedles. For example, the device may include an array of between 2 and 1000 (e.g., between 2 and 100) microneedles. In one embodiment, a device may include between 2 and 10 microneedles. An array of microneedles may include a mixture of different microneedles. For instance, an array may include microneedles having various lengths, base portion diameters, tip portion shapes, spacings between microneedles, drug coatings, etc.

The single microneedle or array of two or more microneedles may extend from the base of the microneedle device at any angle suitable for insertion into the eye. In a particular embodiment, the single microneedle or array of two or more microneedles extend from the base at an angle of about 90 degrees to provide approximately perpendicular insertion of the microneedles into the surface of the eye. In another particular embodiment, the single microneedle or array of two or more microneedles extend from the base at an angle from about 60 to about 90 degrees. In embodiments wherein the microneedle device comprises an array of two or more microneedles, the angle a single microneedle extends from the base may be independent from the angles at which the other microneedles in the array extend from the base of the device.

The microneedle can be fabricated by a variety of methods known in the art or as described in the Examples below. Details of possible manufacturing techniques are described, for example, in U.S. Patent Application Publication No. 2006/0086689 A1 to Raju et al., U.S. Patent Application Publication No. 2006/0084942 to Kim et al., U.S. Patent Application Publication No. 2005/0209565 to Yuzhakov et al., U.S. Patent Application Publication No. 2002/0082543 A1 to Park et al., U.S. Pat. No. 6,334,856 to Allen et al., U.S. Pat. No. 6,611,707 to Prausnitz et al., U.S. Pat. No. 6,743,211 to Prausnitz et al., all of which are incorporated herein by reference for their disclosure of microneedle fabrication techniques.

In a particular embodiment, microneedles would be fabricated on a flexible base substrate. Because the surface of the eye is curved, it would be advantageous in some circumstances to have a base substrate that can bend to conform to the shape of the ocular surface. In another particular embodiment, the microneedles are fabricated on a curved base substrate. The curvature of the base substrate would be designed to conform to the shape of the ocular surface, such that the base substrate would have a radius of curvature substantially the same as the radius of curvature of an ocular tissue surface (e.g., sclera or cornea). For instance, the base substrate may have a radius of curvature between about 0.3 cm and about 0.9 cm, e.g., between 0.5 cm and 0.7 cm. In such an embodiment, the base substrate can serve as a means for controlling the depth and angle of microneedle insertion.

In another particular embodiment, the microneedles may be fabricated such that all or part of the microneedles are adapted to break or dissolve off of the base upon after insertion into the ocular tissue. For example, the microneedle could be designed with one or more stress concentration regions (condition in which a stress distribution has high localized stresses, usually induced by an abrupt change in the shape, e.g., in the vicinity of notches, holes, changes in diameter of a shaft, and so forth) or made brittle at a select location in the microneedle. Alternatively, the microneedle may be fabricated with two or more materials that have different physical or chemical properties that can facilitate failure in vivo., e.g., by dissolution, water uptake/softening, chemical reaction, or the like.

Drug and Drug Formulation

A wide range of drugs may be formulated for delivery to ocular tissues with the present microneedle devices and methods. As used herein, the term "drug" refers to essentially any prophylactic, therapeutic, or diagnostic agent, i.e., an ingredient useful for medical, veterinary, or cosmetic applications. The drug may be selected from suitable proteins, peptides and fragments thereof, which can be naturally occurring, synthesized or recombinantly produced. The drug may be an aptamer. Representative examples of types of drugs for delivery to ocular tissues include antibiotics, antiviral agents, analgesics, anesthetics, antihistamines, anti-inflammatory agents, and antineoplastic agents. Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxbuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegagtanib sodium, ranibizumab, and bevacizumab.

In certain embodiments the drug may be an integrin antagonist, a selectin antagonist, an adhesion molecule antagonist (e.g., Intercellular Adhesion Molecule (ICAM)-1, ICAM-2, ICAM-3, Platelet Endothelial Adhesion Molecule (PCAM), Vascular Cell Adhesion Molecule (VCAM)), or a leukocyte adhesion-inducing cytokine or growth factor antagonist (e.g., Tumor Neucrosis Factor-α (TNF-α), Interleukin-1β (IL-1β), Monocyte Chemotatic Protein-1 (MCP-1) and a Vascular Endothelial Growth Factor (VEGF)), as described in U.S. Pat. No. 6,524,581 to Adamis. In certain other embodiments, the drug may be sub-immunoglobulin antigen-binding molecules, such as Fv immunoglobulin fragments, minibodies, and the like, as described in U.S. Pat. No. 6,773,916 to Thiel et al. In another embodiment, the drug may be a diagnostic agent, such as a contrast agent, known in the art.

The drug typically needs to be formulated for storage and delivery via the microneedle device described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. The excipient may comprise, for example, a polymer, a protein, an amino acid, a sugar or other carbohydrate, a starch, a lipid, or a combination thereof. The drug formulation may be, for example, a liquid solution, a liquid suspension, a gel, or in solid (particulate or monolithic) form. The drug formulation can be tailored to flow through hollow microneedles from a reservoir, can be coated onto the microneedle, can be included/integrated into the microneedle structure, or a combination thereof.

In one embodiment, the drug formulation includes microparticles or nanoparticles of drug suspended in an aqueous or non-aqueous liquid vehicle. The liquid vehicle may be a pharmaceutically acceptable aqueous solution, and optionally may further include a polymer and/or a surfactant. The microparticles or nanoparticles of drug themselves may include an excipient material, such as a polymer, a polysaccharide, a surfactant, etc., which are known in the art to control the kinetics of drug release from particles.

In one embodiment, the fluid drug formulation further includes an agent effective to degrade collagen or GAG fibers in the sclera or corneal stroma, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—injection of administration of the drug. The enzyme and drug are administered at the same site.

In one particular embodiment, the drug formulation may be coated onto microneedles by dip coating, spray coating, or other techniques known in the art, exemplary methods of which are described in PCT Publication No. WO 2006138719 A2 to Gill and Prausnitz, the disclosure of which is incorporated herein by reference in its entirety. Such coatings may be solid or semi-solid. In one embodiment, the coating may be at least partially soluble in the fluids present in the ocular tissue or may be adapted to detach from the microneedles in a substantially intact form. In another embodiment, the drug formulation may comprise a suspension of microparticles or nanoparticles for the controlled release of the drug as described herein.

Control Features for Directing Movement of the Microneedle in the Methods of Use The microneedle device may comprise a means for controllably inserting, and optionally retracting, the microneedle into the ocular tissue. In addition, the microneedle device may include means of controlling the angle at which the at least one microneedle is inserted into the ocular tissue (e.g., by inserting the at least one microneedle into the surface of the ocular tissue at an angle of about 90 degrees).

The depth of microneedle insertion into the ocular tissue can be controlled by the length of the microneedle, as well as other geometric features of the microneedle. For example, a flange or other a sudden change in microneedle width can be used to limit the depth of microneedle insertion. The microneedle insertion can also be controlled using a mechanical micropositioning system involving gears or other mechanical components that move the microneedle into the ocular tissue a controlled distance and, likewise, can be operated, for example, in reverse, to retract the microneedle a controlled distance. The depth of insertion can also be controlled by the velocity at which the microneedle is inserted into the ocular tissue. The retraction distance can be controlled by elastic recoil of the ocular tissue into which the microneedle is inserted or by including an elastic element within the microneedle device that pulls the microneedle back a specified distance after the force of insertion is released.

The angle of insertion can be directed by positioning the microneedle at a first angle relative to the microneedle base and positioning the base at a second angle relative to the ocular surface. In one embodiment, the first angle can be about 90° and the second angle can be about 0°. The angle of insertion can also be directed by having the microneedle protrude from a device housing through a channel in that housing that is oriented at a specified angle.

One skilled in the art may adapt mechanical systems known in the art in combination with the disclosure set forth herein and in the Examples below to devise suitable structures to controllably drive the microneedle insertion, which structures may be manually operable, electromechanically operable, or a combination thereof.

Control of Transport Through Microneedle

The transport of drug formulation or biological fluid through a hollow microneedle can be controlled or monitored using, for example, one or more valves, pumps, sensors, actuators, and microprocessors. For instance, in one embodiment the microneedle device may include a micropump, microvalve, and positioner, with a microprocessor programmed to control a pump or valve to control the rate of delivery of a drug formulation through the microneedle and into the ocular tissue. The flow through a microneedle may be driven by diffusion, capillary action, a mechanical pump, electroosmosis, electrophoresis, convection or other driving forces. Devices and microneedle designs can be tailored using known pumps and other devices to utilize these drivers. In one embodiment, the microneedle device may further include an iontophoretic apparatus, similar to that described in U.S. Pat. No. 6,319,240 to Beck, for enhancing the delivery of the drug formulation to the ocular tissue. In another embodiment the microneedle devices can further include a flowmeter or other means to monitor flow through the microneedles and to coordinate use of the pumps and valves.

The flow of drug formulation or biological fluid can be regulated using various valves or gates known in the art. The valve may be one which can be selectively and repeatedly opened and closed, or it may be a single-use type, such as a fracturable barrier. Other valves or gates used in the microneedle devices can be activated thermally, electrochemically, mechanically, or magnetically to selectively initiate, modulate, or stop the flow of material through the microneedles. In one embodiment, the flow is controlled with a rate-limiting membrane acting as the valve.

The present invention may be further understood with reference to the following non-limiting examples.

EXAMPLE 1

Drug-Coated Solid Microneedles

Single solid microneedles were fabricated using an infrared laser to cut microneedles from 75 micron thick stainless steel sheets. To deburr and sharpen the microneedle edges, electropolishing was done in a 1:3:6 v/v mixture of water:phosphoric acid:glycerine at 70° C. The final microneedle dimensions were 500 µm in length, 50×200 µm in cross section at the base, and 55° in tip angle. For in vivo rabbit experiments, the microneedles were modified to 500 µm in length, 50×100 µm in cross section at the base, and 45° in tip angle, to avoid penetration through the thinner rabbit corneal tissue. To facilitate handling microneedles using forceps during insertion into tissue, an extended metal substrate was attached to the needle base, which measured 1 cm in length, 4 mm in width and 50 µm in thickness, was included in the needle design.

The microneedles were coated at room temperature using a dip coating method and an aqueous coating solution. The aqueous coating solution contained 10% (w/v) poly-vinyl-pyrrolidone (1300 kDa) and 0.05% (w/v) sulforhodamine, 1.0% (w/v) FITC-labeled bovine serum albumin, or 0.05% (w/v) YOYO-3-labeled gWiz luciferase plasmid DNA for in vitro experiments. The aqueous coating solution contained 0.5% (w/v) sodium fluorescein and 10% (w/v) pilocarpine hydrochloride for in vivo experiments. The thickness of the coating was approximately 5 to 15 µm, and the dose coated onto the microneedles was measured by dissolving the coating into deionized water and measuring the compound concentration using fluorescence spectrometry or UV spectrometry.

EXAMPLE 2

In Vitro Drug Delivery to Human Sclera

Human sclera was obtained from the Georgia Eye Bank with the approval of the Georgia Tech IRB. Pieces of the scleral tissue were cut to a size of 0.7×0.7 cm using surgical scissors and rinsed with deionized water. Adherent tissues associated with the retina, choroid, and episclera were removed from the scleral tissue with a cotton swab and the scleral tissue was then placed on top of a hemispherical surface (0.6 cm in radius), which simulated the curvature of the ocular surface.

Uncoated single microneedles from Example 1 were manually inserted approximately half way into the sclera tissue and then removed. The insertion site was stained with a blue tissue dye and imaged by brightfield and fluorescence microscopy to assess the site and extent of delivery.

Figure 7A:
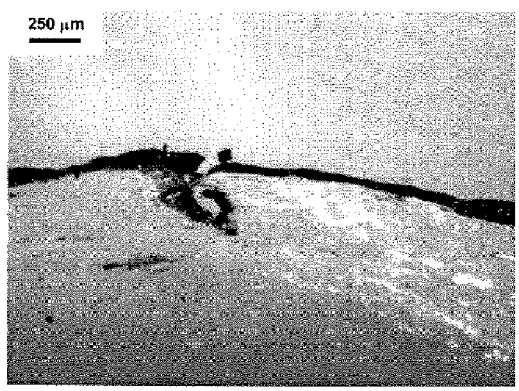
FIGS. 7A and 7B are brightfield microscopic images of histological sections of human sclera pierced with a solid microneedle and subsequently stained with a blue tissue marking dye and for a sulforhadamine-coated microneedle, respectively.
Figure 7B:
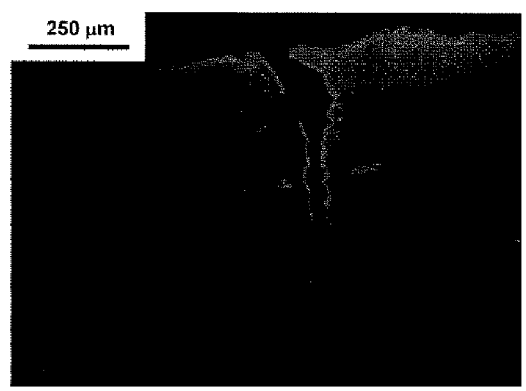

The microneedles were found to be sufficiently strong and sharp to penetrate into the sclera without bending or breaking (data not shown). Within two minutes, the microneedle coating dissolved off and was deposited within the sclera, as shown in FIGS. 7A-B. The figures also show that the insertion site penetrated approximately 300 µm deep into the sclera and that the coating was deposited throughout the microneedle hole, as well as some deposition along the sclera surface.

Coated microneedles from Example 1 then were tested to determine whether the coating remained intact during insertion and rapidly dissolved off the microneedles within the tissue. The sodium fluorescein-coated microneedles from Example 1 were manually inserted into sclera tissue, left within the tissue for 20 seconds to allow the coating solution to dissolve off and then removed. The insertion site was stained with a blue tissue dye and imaged by brightfield and fluorescence microscopy to assess the site and extent of delivery (FIG. 7A).

The sulforhodamine coating was found to be deposited to a large extent within the microneedle hole, showing that the coating was rapidly dissolved off the needle shaft within the sclera (FIG. 7B). There also was some sulforhodamine deposited on the tissue surface. Similar results were obtained for experiments conducted using bovine serum albumin-coated microneedles (data not shown).

The microneedles were examined using brightfield microscopy to identify any mechanical defects after insertion. Neither needle breakage nor bending were detected, which suggests that the microneedles were sufficiently strong and sharp to penetrate into rigid scleral and corneal tissues. The bottom half of the microneedle shafts, however, generally showed evidence of residual coating, which likely was due to the incomplete microneedle insertion into the tissue.

EXAMPLE 3

In Vivo Drug Delivery to Rabbit Cornea

New Zealand white rabbits were anesthetized using intramuscular injection of ketamine and xylazine. Then, the fluorescein-coated microneedles from Example 1 were inserted into the upper region of the cornea and left within the tissue for two minutes. After removal of the microneedle, fluorescein concentration in the anterior segment of the eye was measured by spectrofluorometry for $\leq 24$ h (n=4).

Figure 8A:
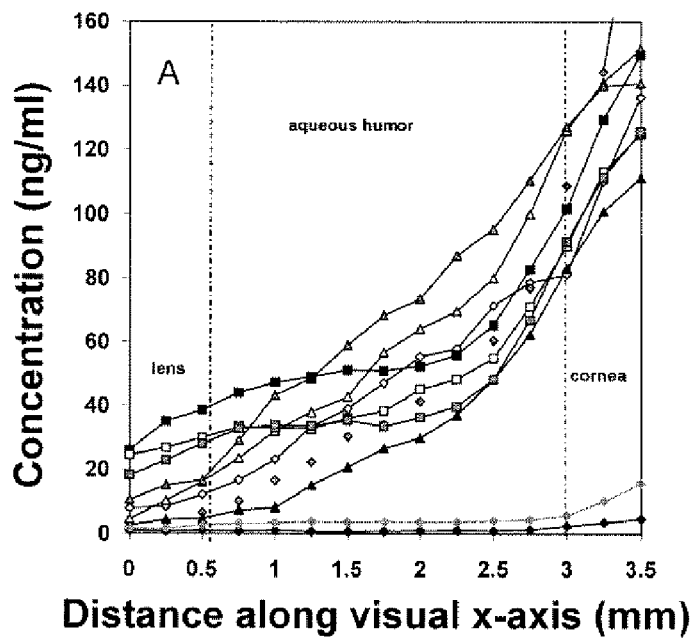
FIGS. 8A and 8B illustrate the fluorescein concentration profiles in a rabbit eye over time as an average value in the aqueous humor as a comparison of microneedle (gray bars) and topical delivery (black bars), respectively.
Figure 8A:
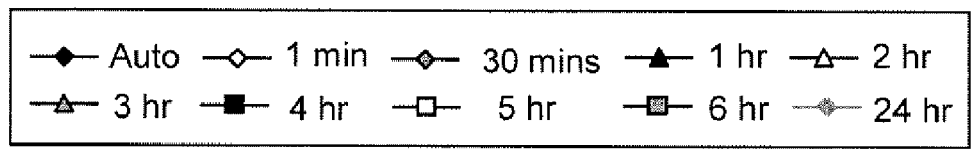
Figure 8B:
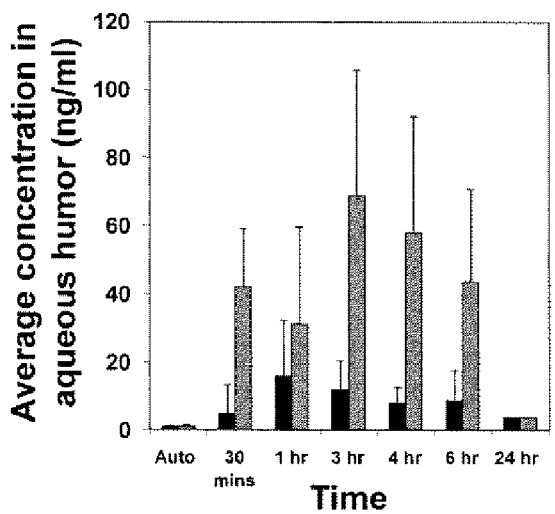

To facilitate imaging and fluorometric analysis, fluorescein was delivered to the cornea, rather than the sclera, and monitored fluorescein concentration in the anterior of the rabbit eye for 24 hours after insertion of a microneedle coated with 280 ng fluorescein. As shown in FIGS. 8A-B, fluorescein concentration was measured over time as a function of the distance along the visual axis in the anterior segment of the eye from the cornea to lens. Prior to microneedle insertion, only small amounts of background fluorescence were detected in the aqueous humor. At the first measurement made just 1 min after microneedle insertion, a sharp increase of intraocular fluorescein concentration was observed. FIG. 5A shows that the measured fluorescein concentration in the anterior segment further increased, reaching a peak after 3 hours, and then gradually decreased to background levels within 24 hours. These results suggest that the fluorescein coating dissolved off the microneedle (within seconds) into a depot formed within the cornea, which steadily released fluorescein into the anterior segment of the rabbit eye for hours.

For comparison, a control experiment was performed using a conventional topical application with a 10-fold larger fluorescein dose (i.e., 2.8 µg), and similarly measured the fluorescein concentration in the eye over time. As shown in FIG. 8B, there was delivery of only very low levels of fluorescein to the aqueous humor after topical delivery.

The delivery of a bioactive drug was measured by individually inserting five pilocarpine-coated microneedles (1.1±0.5 µg pilocarpine per microneedle for a total of 5.5 µg pilocarpine) half way into the rabbit cornea under anesthesia and then removed after 20 seconds. The microneedles were each spaced approximately 4 mm apart in a radial pattern around the center of the cornea. The pupil diameter was measured over time to assess pilocarpine-induced constriction. As a negative control, pupil size of the untreated eye was measured at the same time points. As positive controls, a 50 µl drop of 0.01% (w/v) pilocarpine solution was topically applied to the eye (5 µg pilocarpine) and a 50 µl drop of 1% (w/v) ophthalmic pilocarpine solution (500 µg pilocarpine) was topically applied to the eye.

Figure 9:
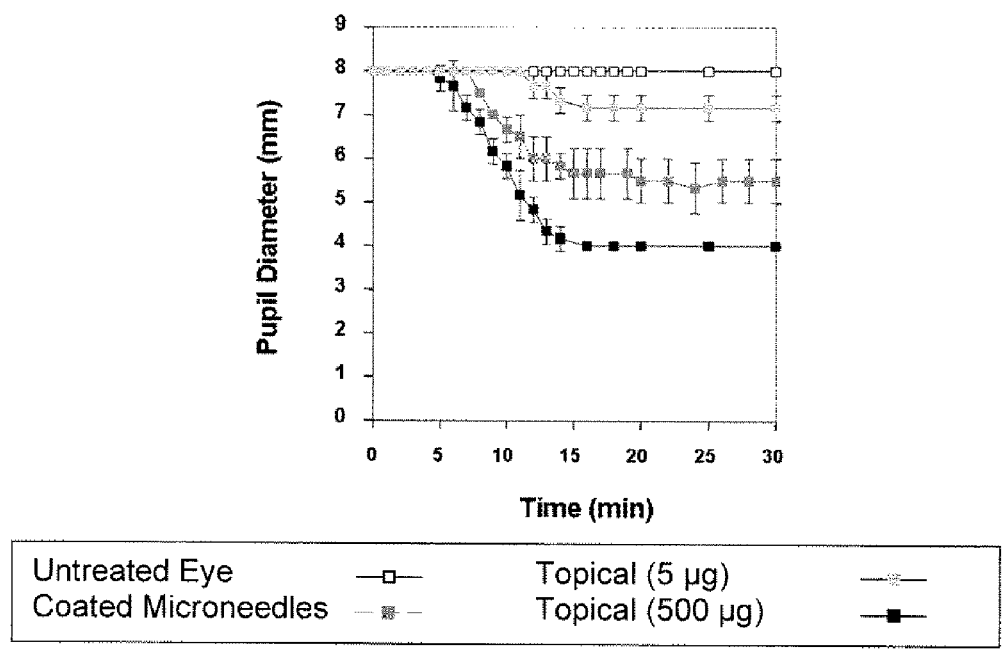
FIG. 9 is a graph showing the changes in the pupil diameter of a rabbit over a time for an untreated eye and for eyes treated with pilocarpine coated microneedles or topical applications of pilocarpine.

In the negative control, pupil size remained unchanged over the 30 min observation period. In contrast, microneedle delivery of pilocarpine caused pupil constriction from 8 mm to 5.5 mm diameter within 15 min. Topical delivery of an almost identical dose of pilocarpine caused pupil constriction to just 7 mm with slower kinetics. As a positive control, topical delivery of a pilocarpine dose more than 90 times greater than the microneedle dose caused pupil constriction to 4 mm with similar kinetics. ANOVA analysis showed that the changes in pupil diameter over time were all different from each other among the four experimental conditions (p<0.0001). See FIG. 9.

EXAMPLE 4

Bioavailability of In Vivo Drug Delivery to Rabbit Cornea

A one-compartment pharmacokinetic analysis of the in vivo fluorescein delivery data obtained in Example 3 was conducted to determine the total dose of fluorescein delivered into the eye after microneedle treatment. Using the anterior segment as the compartment in a one-compartment model, a mass balance on fluorescein in the aqueous humor of the rabbit eye was performed $$M_{in} = M_{out} + M_{acc} \tag{EQ.1}$$

where $M_{in}$ is the fluorescein mass inflow rate from the cornea, $M_{out}$ is the fluorescein outflow rate via aqueous humor drainage, and $M_{acc}$ is the fluorescein accumulation rate in the aqueous humor. This approach neglects fluorescein outflow by routes other than aqueous humor drainage, such as uptake into the lens.

The fluorescein outflow rate can be calculated as:

$$M_{out} = C_{fl} \cdot v_{aq} \tag{EQ.2}$$

where $C_{fl}$ is the fluorescein concentration in the aqueous humor, which is assumed to be spatially uniform (which is an imperfect assumption) and therefore equal to the average experimental measurement, and $v_{aq}$ is the aqueous humor volumetric flow rate, which is reported as 4.2-4.5 µl/min in the rabbit eye (see Fatt & Wissman *Physiology of the Eye. An Introduction to the Vegataitive Functions,* 2nd ed (1992)).

The fluorescein accumulation rate can be estimated as $$M_{acc} = \frac{d(V_{aq} C_{fl})}{dt} \cong \frac{V \Delta C_{fl}}{\Delta t} \tag{EQ. 3}$$

where $\Delta C_{fl}$ is the change of fluorescein concentration in the aqueous humor between two measurements; $V_{aq}$ is the aqueous humor volume, which is approximately 0.3 ml in the rabbit eye; (See Conrad & Robinson, *J Pharm Sci* 66:219-224 (1977)). and $\Delta t$ is the time between measurements.

By substituting EQ. 2 and EQ. 3 into EQ. 1, the fluorescein mass inflow rate is estimated as $$M_{in} = C_{fl}v_s + \frac{V \Delta C_{fl}}{\Delta t} \quad \text{(EQ. 4)}$$

and the total amount of fluorescein entering the aqueous humor ($M_{in,totals}$) is equal to $$M_{in,total} = \sum_{n}^{i} M_{in_n} \Delta t_n \quad \text{(EQ. 5)}$$

where i is the number of measurement points and n is the corresponding measurement point number. In this endpoint calculation, the total amount of fluorescein that entered the aqueous humor equals the total amount that left the aqueous humor and the accumulation terms goes to zero. Bioavailability was determined as the ratio of the total amount of fluorescein entering the aqueous humor and the amount of fluorescein coated onto the microneedle.

The total amount of fluorescein delivered into the aqueous humor was calculated to be 196±15 ng, or approximately 69% of the dose of fluorescein coated on the microneedle. A similar pharmacokinetic analysis of the data for topically applied fluorescein yielded a bioavailability of just 1%.

To validate these calculations, in vitro experiments were conducted. The amount of fluorescein delivered into rabbit cadaver cornea from fluorescein-coated microneedles and the amount of fluorescein remaining on the needle after insertion were measured. An average of 74±27% of the fluorescein coated onto the microneedle was delivered into the cornea in vitro, similar to the result obtained from the in vivo pharmacokinetic analysis.

It is believed that the fluorescein was released from the microneedle to form a depot in the corneal tissue, which provided subsequent drug release with a bioavailability of approximately 70%. Thus, the microneedle delivery provided a 70-fold increase in bioavailability relative to topical application. It is believed that the remaining fluorescein either remained adherent to the microneedle or might have been washed away by the tear fluid.

A similar analysis of pilocarpine bioavailability was conducted. Topical delivery of 5.0 μg of pilocarpine resulted in pupil constriction of 1 mm and topical delivery of 500 μg of pilocarpine resulted in pupil constriction of 4 mm. Microneedle delivery 5.5 μg of pilocarpine resulted in pupil constriction of 2.5 mm, or the equivalent of a topical delivery of approximately 250 μg of pilocarpine (assuming a linear dose-response relationship and carrying out linear interpolation of the two topical delivery doses). Thus, the microneedle delivery of pilocarpine provided a 45-fold increase in pilocarpine bioavailability relative to topical administration.

EXAMPLE 5

Non-Coated Microneedle Inserted into Rabbit Cornea

To assess the safety of microneedle insertion into the eye, the single, non-coated microneedle of Example 1 was inserted into the cornea of an anesthetized rabbit in vivo. At 0, 1, 2, 3, 4, and 24 hours after insertion, the eye was examined by a clinical opthalmologist using a slit lamp to identify (i) whether a hole remained in the cornea at the site of insertion and (ii) whether any inflammatory response was present, as indicated by the occurrence of anterior chamber cells or flare (as described by Shah et al., *Br J Ophthalmol* 75:348-52 (1991)). Before each examination, a drop of fluorescein solution was applied topically to stain sites of corneal damage, in order to identify the insertion hole.

A small abrasion was identified at the site of microneedle insertion; however, evidence of the insertion wound was no longer visible after 3 hours, indicating a resealing of the hole, perhaps by epithelial cell migration and restitution (as described by Coke & Podolsky, *Baillieres Clin Gastroenterol* 10:393-405 (1996)). There was no evidence of an inflammatory response at any time point as shown by a lack of anterior chamber cells and flare responses.

EXAMPLE 6

Hollow Glass Microneedles

Single, hollow, glass microneedles were fabricated using a micropipette puller as previously described by McAllister, et al., *Proc. Nat'l Acad. Sci. U.S.A.* 100:13755-60 (2003). Fire-polished borosilicate glass pipettes (outer diameter of 1.5 mm, inner diameter of 0.86 mm, B150-86-15, Sutter Instrument, Novato, Calif.) were pulled using a micropipette puller (P-97, Sutter Instrument) and detached into two microneedles at desired settings. These blunt-tip microneedles then were beveled at a setting of 20 degree tip angle using a glass grinder (BV-10, Sutter Instrument) and then cleaned sequentially in a chromic acid bath, DI water bath, and acetone bath for 15 seconds each. The glass microneedles had a tip opening of 100 μm in length and 40 μm in diameter, and an angle of 25 degrees.

EXAMPLE 7

In Vitro Drug Delivery to Human Sclera

The single microneedles of Example 6 were inserted into human cadaver sclera at a constant pressure (5, 10, 15, 20, and 25 psi) and used to deliver a sulforhodamine solution. Sulforhodamine (558 Da; Molecular Probes, Eugene, Oreg.), which serves as a model drug and a visual marker for fluid flow, was added to phosphate buffered saline (PBS) to make a $1 \times 10^{-3}$ M sulforhodamine solution and was loaded into a glass syringe fluidly connected to the glass microneedle as described in Wang, et al., *Diabetes Tech & Ther* 7: 131-41 (2005). The microneedles were initially inserted into the tissue at a depth of 700-1080 μm, and retracted out of the tissue in increments of 60 μm during the solution injection. The volumetric delivery of sulforhodamine solution was monitored by the movement of the gas-fluid meniscus in the glass syringe, and the differences were recorded between each retraction. The infusion was immediately stopped when a retraction caused leakage of sulforhodamine solution to be first seen on the surface of the tissue.

Generally, the distribution of the sulforhodamine solution appeared in a circular shape, with a diameter ranging from millimeters up to one centimeter, depending on infusion conditions (data not shown). The insertion of a single microneedle 720 μm into the middle region of a scleral piece, and the retraction 200 μm to infuse sulforhodamine solution into the tissue resulted in an insertion pathway with a depth of 300 μm and an insertion gap having the shape of the needle tip. The difference between the needle penetration depth and the insertion depth that occurred is believed to have been caused by elastic deformation of the tissue during insertion.

In the human eye, the sclera is relatively thick near the limbus (0.53±0.14 mm); it thins at the equator (0.39±0.17 mm) and becomes substantially thicker near the optic nerve (0.9 to 1.0 mm) (Olsen, et al., *Am J Opthalm* 125:237-41 (1998)). To examine the effect of scleral thickness on volume delivery, the sclera was divided into 3 different regions around the globe: front (near the limbus), middle (at the equator), and back (near the optic nerve). The microneedles were inserted into each region of the sclera at a controlled depth (720-1080 μm), and then partially retracted. Each retraction displacement was 60 μm and lasted 3 minutes. Since the scleral tissue at the equator is thinner compared to that near the limbus and the optic nerve, typically less retraction (209±92 μm) in the middle region was used comparing to that in the front (287±182 μm) and in the back regions (262±145 μm).

Essentially no solution was delivered into the tissue after the initial insertion in all experiments. Upon further retraction from 200 to 300 μm the delivery was achieved at volumes of 10 to 15 μL from individual microneedles. Not wishing to be bound by any theory, it is believed that these observations can be explained by the elastic nature of the scleral fibers. The scleral fibers are known to be elastic (Bourges, et al., *Invest Opthalm & Visual Sci* 44:3562-69 (2003)), and the elastic system appears to be largely confined to the deeper layers in the sclera (Raspanti, et al., *J Anatomy* 181(Part 2): 181-87 (1992)), which could cause the zero volumetric delivery after the initial insertion. After the needle penetrated into inner portion of the sclera, the fibers were deformed due to the compression of needle tip and blocked the needle tip opening, thereby stopping the solution flow. As the microneedle was retracted back into the upper layer, where the fibers were less elastic, opening spaces between the needle and collagen fibers began to form, allowing the solution to spread within the tissue.

EXAMPLE 8

In Vitro Delivery of Nanoparticles & Microparticles to Human Sclera

Experiments were conducted to evaluate the ability of the hollow microneedles of Example 6 to deliver nanoparticles or microparticles into the sclera. Each microneedle was preloaded with 20 μl of the nanosphere or microsphere suspension, inserted into each region on the sclera, and delivered into the tissue using the insertion and retraction procedures of Example 7.

Nanospheres comprised Nile Red encapsulated within poly-lactic acid (PLA) (effective diameter of 278±13 nm) particles (courtesy of Dr. Uday Kompella, University of Nebraska). PBS solutions of the nanoparticles were prepared with solid contents of 0.5, 1, 5, and 10 wt %, vortexed to break up aggregates, and delivered into the sclera at 15 psi.

PBS solutions containing solid latex, fluorescein-labeled microspheres (1.0 micron in diameter, Polysciences Inc., Warrington, Pa.) were prepared with solid contents of 0.3, 1.3, and 2.6 wt % for infusion into sclera. A drop of 5 μl polyoxyethylenesorbitan monooleate (Tween 80, Sigma Chemical Co., St. Louis, Mo.) was added to each ml solution to reduce the surface tension and enhance the microparticle stability within the suspension. The mixture was vortexed and ultrasonicated to ensure the microspheres were suspended without aggregating within the solution.

The nanoparticles were successfully delivered within the tissue; however, unlike the results from sulforhodamine infusion experiments, the nanoparticles did not spread widely within the tissue. Concentrated particle regions were evident around the microneedle insertion gap, which suggested that the particles filled the spaces between collagen fibers. The amount of nanoparticles infused into the scleral tissue increased as the concentration of particles in the donor solution increased in each region of the sclera. At lower nanosphere concentrations, the distribution of the particles appeared to be localized around the needle insertion site. At the higher concentrations, the particles spread further away from the insertion site. In each experiment, a large majority of the suspension was delivered into the sclera with only a tiny amount, up to a couple of microliters, leaking onto the scleral surface.

The microparticles were not delivered to the tissue in any significant number in this instance. The microparticles appeared to clog the tip of the hollow microneedles, though it is believed that the presence of scleral tissue played a critical role in blocking flow. The collagen fibers in the human sclera are reported to vary from 160 nm to 220 nm in diameters (Raspanti, et al., *J. Anatomy* 181(Part 2): 181-87 (1992)), and their center-to-center spacing varies between 250 nm and 280 nm (Edwards & Prausnitz, *AIChE* 44:214-25 (1998)), corresponding to an edge-to-edge spacing of 410 nm to 500 nm. Accordingly, it is believed that the nanometer-scale spacing between scleral collagen fibers might serve as a barrier during microparticle delivery, thereby restricting the ability of large-sized microspheres to pass into the scleral tissue. The non-collagenous proteins also may play a role in controlling transport in the sclera. These proteins make up 10% of the scleral dry weight (Fattand & Wissman, *Physiology of the Eye. An Introduction to the Vegatatve Function*, Buterworth-Heinemann, Boston, Mass. (1992)), and some of them are associated with glycosaminoglycans (GAGs) and together form proteoglycan complexes (the GAGs form side chains that are chemically linked to a core protein) (Edwards & Prausnitz (1998)). The junctions of these proteoglycan complexes therefore also may play an important role in microparticle delivery.

EXAMPLE 9

In Vitro Drug Delivery of Microparticles with Collagenase or Hyaluronidase

Two types of experiments were performed to examine the effect of hyaluronidase, an enzyme known to break down the GAGs in the scleral extracellular matrixes, or collagenase type I, which is known to break down type I collagen fibers, on scleral delivery using the hollow microneedles of Example 6. In one experiment, the scleral tissue was soaked in a 200 U/ml hyaluronidase solution (Vitrase, 200 U/ml, ISTA Pharmaceuticals, Irvine, Calif.) or a collagenase type I solution for 1 hour prior to microneedle injection and later infusion experiments were performed. In the second experiment, a hyluronidase solution or a collagenase type I solution was mixed with the injectable solution and delivered into the sclera by the hollow microneedles.

A significantly larger dose of microspheres was delivered into each region of the scleral tissue that was soaked in the hyaluronidase solution prior to the infusion experiment. The same effect also took place in the hyaluronidase-mixed infusion tests, thereby indicating that the effect of hyaluronidase is extremely rapid. Accordingly, it is believed that by breaking down the ground substance in the sclera matrix larger particles, such as microparticles, can be delivered into the scleral tissue.

A significantly larger dose of microspheres also was delivered into each region of the scleral tissue with the collagenase experiments (data not shown). It is believed that the tight architecture of the collagen fibers served as a critical barrier in micron-sized particle delivery.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method of administering a drug to an eye of a patient, comprising:
    inserting at least one hollow microneedle into the sclera or corneal stroma of the eye without penetrating across the sclera or corneal stroma; and
    infusing a fluid drug formulation through the at least one hollow microneedle and into the sclera or cornea, wherein the fluid drug formulation comprises a drug.

2. The method of claim 1, further comprising, after the insertion step and before and/or during the step of infusing, partially retracting the at least one hollow microneedle from the sclera or corneal stroma.

3. The method of claim 2, wherein the step of infusing is performed after the step of retracting the at least one microneedle out of the sclera or corneal stroma.

4. The method of claim 1, wherein the step of inserting further comprises substantially simultaneously inserting a second hollow microneedle into the sclera or corneal stroma without penetrating across the sclera or corneal stroma, and the step of infusing further comprises infusing the fluid drug formulation through the second hollow microneedle and into the sclera or corneal stroma, wherein the at least one hollow microneedle and the second hollow microneedle are part of a device which comprises an array of two or more microneedles.

5. The method of claim 1, wherein the fluid drug formulation comprises a suspension of microparticles or nanoparticles for controlled release of the drug.

6. The method of claim 1, wherein the at least one hollow microneedle is inserted into the surface of the sclera or corneal stroma at an angle of about 90 degrees.

7. The method of claim 1, wherein the at least one hollow microneedle comprises a metal.

8. The method of claim 1, wherein the at least one hollow microneedle is rotated or vibrated during the step of inserting.

9. The method of claim 1, wherein the step of infusing comprises driving the fluid drug formulation using a pressure gradient or an electric field.

10. The method of claim 1, for use in the treatment of uveitis, glaucoma, diabetic macular edema, age-related macular degeneration, corneal infection, or cytomegalovirus retinitis.

11. The method of claim 1, wherein the fluid drug formulation further comprises an agent effective to degrade collagen or glycosaminoglycan fibers in the sclera or corneal stroma.

12. The method of claim 11, wherein the agent comprises an enzyme selected from the group consisting of a hyaluronidase, a collagenase, or a combination thereof.

13. The method of claim 2, wherein the steps of inserting and retracting the at least one hollow microneedle form a pocket in the sclera or corneal stroma.

14. The method of claim 1, wherein the step of infusing creates a drug depot in the sclera or corneal stroma for sustained release of the drug from the drug depot after the step of infusion is completed.

15. A method of administering a drug to an eye of a patient, comprising:
    inserting at least one solid microneedle into the sclera or corneal stroma of the eye without penetrating across the sclera or corneal stroma, wherein the at least one solid microneedle comprises a first quantity of a drug formulation and the step of inserting causes the at least one solid microneedle to form a pocket in the sclera or corneal stroma; and
    releasing at least part of the first quantity of the drug formulation into the pocket to form a drug depot in the sclera or corneal stroma, whereby a drug in the drug formulation subsequently is released from the drug depot.

16. The method of claim 15, wherein the step of inserting further comprises substantially simultaneously inserting a second solid microneedle into the sclera or corneal stroma without penetrating across the sclera or corneal stroma, the second solid microneedle comprising a second quantity of the drug formulation, and wherein the step of inserting causes the second solid microneedle to form a second pocket in the sclera or corneal stroma,
    wherein the step of releasing further comprises releasing the second quantity of the drug formulation into the second pocket to form a second drug depot in the sclera or corneal stroma, whereby subsequently the drug is released from the second drug depot into the eye,
    wherein the at least one solid microneedle and the second solid microneedle are part of a device which comprises an array of two or more microneedles.

17. The method of claim 15, further comprising completely withdrawing the at least one solid microneedle from the sclera or corneal stroma after the step of inserting, wherein the drug depot provides sustained release of the drug after the at least one solid microneedle has been completely withdrawn.

18. The method of claim 15, wherein the at least one solid microneedle comprises a solid or semi-solid coating which comprises the drug formulation.

19. The method of claim 18, wherein the step of releasing comprises at least partially dissolving the coating off of the at least one solid microneedle into fluids present in the sclera or corneal stroma.

20. The method of claim 15, wherein the step of releasing comprises breaking or dissolving all or part of the at least one solid microneedle, which includes the drug formulation, off of a base to which the at least one solid microneedle is connected prior to said breaking or dissolving.

21. The method of claim 15, wherein the drug formulation comprises microparticles or nanoparticles which comprise a drug for controlled release.

22. The method of claim 15, wherein the at least one solid microneedle is inserted into the surface of the sclera or corneal stroma at an angle of about 90 degrees.

23. The method of claim 15, wherein the at least one solid microneedle comprises a metal.

24. The method of claim 15, wherein the at least one solid microneedle comprises a polymer.

25. The method of claim 15, wherein the at least one solid microneedle is rotated or vibrated during the step of inserting or during the step of releasing.

26. The method of claim 15, further comprising driving the drug into or through the sclera or corneal stroma using an electric field or acoustic energy.

27. The method of claim 15, for use in the treatment of uveitis, glaucoma, diabetic macular edema, age-related macular degeneration, corneal infection, or cytomegalovirus retinitis.

28. The method of claim 1 or 15, wherein the drug from the drug depot is delivered to choroidal or retinal tissues.

29. The method of claim 1 or 15, wherein the drug is delivered to the ciliary body or the trabecular meshwork.

30. The method of claim 1 or 15, wherein the drug is delivered to the aqueous humor or the vitreous humor.

31. A method of extraction from a tissue of the eye comprising:
    inserting at least one microneedle into the sclera or corneal stroma, without penetrating across the sclera or corneal stroma; and
    withdrawing a biological fluid, tissue, or molecule sample from the sclera or corneal stroma with the at least one microneedle.

32. A microneedle device for delivery of a drug to the eye comprising:
    an array of two or more microneedles extending from a base;
    means for controllably inserting the two or more microneedles into the sclera or corneal stroma without penetrating across the sclera or corneal stroma; and
    means for depositing a drug formulation in the sclera or corneal stroma to form a drug depot for subsequent release to an ocular tissue.

33. The device of claim 32, wherein the drug depot provides extended or sustained release of a drug after the two or more microneedles have been completely withdrawn from the sclera or corneal stroma.

34. The device of claim 33, wherein the drug formulation comprises microparticles or nanoparticles which provide controlled release of the drug.

35. The device of claim 32, wherein the two or more microneedles are solid.

36. The device of claim 35, wherein the means for depositing comprises a coating on the two or more microneedles, wherein the coating comprises the drug formulation.

37. The device of claim 36, wherein the coating is solid or semi-solid.

38. The device of claim 37, wherein the coating is at least partially soluble in fluids present in the sclera or corneal stroma.

39. The device of claim 32, wherein all or part of the two or more microneedles are adapted to break or dissolve off of the base in the sclera or cornea.

40. The device of claim 32, wherein the two or more microneedles comprise a metal.

41. The device of claim 32, wherein the two or more microneedles comprise a polymer.

42. The device of claim 32, wherein the two or more microneedles extend from the base at an angle of about 90 degrees to provide approximately perpendicular insertion of the microneedles into the surface of the sclera or corneal stroma.

43. The device of claim 32, wherein the base has either a fixed radius of curvature substantially the same as the radius of curvature of the surface of a sclera or corneal stroma, or is elastically deformable to fit the radius of curvature of the surface of a sclera or corneal stroma.

44. The device of claim 32, wherein the two or more microneedles are hollow.

45. The device of claim 44, wherein the means for depositing comprises a fluid drug formulation, a source reservoir for the fluid drug formulation, and an infusion means for driving the fluid drug formulation from the source reservoir into the pocket.

46. The device of claim 45, wherein the infusion means comprises a pump or syringe.

47. The device of claim 45, wherein the fluid drug formulation further comprises an agent effective to degrade collagen or glycosaminoglycan fibers in the sclera or corneal stroma.

48. The device of claim 47, wherein the agent comprises an enzyme selected from the group consisting of a hyaluronidase, a collagenase, or a combination thereof.

49. The device of claim 45, wherein the fluid drug formulation comprises a suspension of microparticles or nanoparticles which comprise a drug for controlled release.

50. The device of claim 32, wherein the portion of the microneedles that is designed to insert into the sclera or corneal stoma has a maximum cross-sectional width or diameter between 50 microns and 400 microns.

51. The device of claim 32, wherein the portion of the microneedles that is designed to insert into the sclera or corneal stoma has length between 50 microns and 1000 microns.

52. A microneedle device for delivery of a drug to the eye comprising:
    at least one solid microneedle extending from a base;
    means for controllably inserting the at least one solid microneedle into the sclera or corneal stroma without penetrating across the sclera or corneal stroma; and
    a drug formulation which comprises a drug, wherein the device is adapted to deposit the drug formulation into the sclera or corneal stroma to form a drug depot for controlled release of the drug to an ocular tissue.

* * * * *